(12) United States Patent
Chan et al.

(10) Patent No.: US 12,116,617 B2
(45) Date of Patent: *Oct. 15, 2024

(54) MASS SPECTROMETRY METHOD FOR MEASURING THIAMINE IN BODY FLUID

(71) Applicant: Quest Diagnostics Investments Incorporated, Wilmington, DE (US)

(72) Inventors: Sum Chan, San Clemente, CA (US); Qibo Jiang, Los Angeles, CA (US); Richard E. Reitz, Las Vegas, NV (US)

(73) Assignee: Quest Diagnostics Investments Incorporated, Wilmington, DE (US)

( * ) Notice: Subject to any disclaimer, the term of this patent is extended or adjusted under 35 U.S.C. 154(b) by 432 days.

This patent is subject to a terminal disclaimer.

(21) Appl. No.: 16/989,545

(22) Filed: Aug. 10, 2020

(65) Prior Publication Data
US 2020/0370091 A1 Nov. 26, 2020

Related U.S. Application Data

(63) Continuation of application No. 16/036,340, filed on Jul. 16, 2018, now Pat. No. 10,738,344, which is a continuation of application No. 13/724,839, filed on Dec. 21, 2012, now abandoned, which is a continuation of application No. 11/869,657, filed on Oct. 9, 2007, now abandoned.

(51) Int. Cl.
*C12Q 1/42* (2006.01)
*G01N 33/82* (2006.01)

(52) U.S. Cl.
CPC ............... *C12Q 1/42* (2013.01); *G01N 33/82* (2013.01)

(58) Field of Classification Search
CPC .................................. G01N 33/82; C12Q 1/42
See application file for complete search history.

(56) References Cited

PUBLICATIONS

Airth R.L., et al., "Simultaneous Determination of Thiamine and Pyrithiamine," Analytical Biochemistry, 1962, vol. 3, pp. 383-395.
Bartolucci G., et al., "Liquid Chromatography Tandem Mass Spectrometric Quantitation of Sulfamethazine and its Metabolites: Direct Analysis of Swine Urine by Triple Quadrupole and by Ion Trap Mass Spectrometry," Rapid Communications in Mass Spectrometry, 2000, vol. 14 (11), pp. 967-973.
Batifoulier F., et al., "Determination of Thiamine and Its Phosphate Esters in Rat Tissues Analyzed As Thiochromes on a RP-Amide C16 Column," Journal of Chromatography B,, 2005, vol. 816 (1-2), pp. 67-72.
Bettendorff L., et al., "Discovery of a Natural Thiamine Adenine Nucleotide," Nature Chemical Biology, 2007, vol. 3 (4), pp. 211-212.
Brown S.M., et al., "Fast Atom Bombardment and Secondary !no Mass Spectra of Thiamine Hydrochloride," Organic Mass Spectrometry, 1989, vol. 24, pp. 297-302.
Brown S.M., et al., "Mechanisms in Secondary Ion Mass Spectrometry: Sputtering of Preformed Ions and Reactions of Itinerant Protons," Proceedings of the Indiana Academy of Sciences, 1987, vol. 97, pp. 165-169.
Careri M., et al., "Review-Overview of the Applications of Liquid Chromatography-Mass Spectrometry Interfacing Systems in Food Analysis; Naturally Occurring Substances in Food," Journal of Chromatography A, 1998, vol. 794, pp. 263-297.
Chen P. et al., "LC/UV/MS-MRM for the Simultaneous Determination of Water-Soluble Vitamins in Multivitamin Dietary Supplements," Analytical Bioanalytical Chemistry, 2007, vol. 387 (7), pp. 2441-2448.
Diorio A.F. et al., "The Pathways of Thiamine Biosynthesis: Spearation, Purification, and Identification of Some Precursors of the Pyrimidine Moiety of Thiamine Produced By Neurospora Crassa Auxotrophs," The Journal of Biological Chemistry, 1968, vol. 243 (15), pp. 4006-4012.
Examiner's Answer mailed Jun. 6, 2012 for U.S. Appl. No. 11/869,657, filed Oct. 9, 2007.
Examiner's Answer to Appeal Brief mailed Jan. 27, 2017 for U.S. Appl. No. 13/724,839, filed Dec. 21, 2012.
Final Office Action mailed Sep. 5, 2014 for U.S. Appl. No. 13/724,839, filed Dec. 21, 2012.
Final Office Action mailed Dec. 10, 2015 for U.S. Appl. No. 13/724,839, filed Dec. 21, 2012.
Final Office Action mailed Mar. 21, 2011 for U.S. Appl. No. 11/869,657, filed Oct. 9, 2007.
Heudi O., et al., "Separation of Water-Soluble Vitamins by Reversed-Phase High Performance Liquid Chromatography with Ultra-Violet Detection: Application to Polyvitaminated Premixes," Journal of Chromatography A, 2005, vol. 1070 (1-2), pp. 49-56.
Kozik A., et al., "Ion-Pair Reversed-Phase High-Performance Liquid Chromatographic Method for the Separation of A Set of Unphosphorylated Thiamine-Related Compounds," Journal of Chromatography, 1993, vol. 648, pp. 349-356.
Liu J.Y., et al., "Pyrithiamine as a Substrate for Thiamine Pyrophosphokinase," The Journal Of Biological Chemistry, 2006, vol. 281 (10), pp. 6601-6607.
Liu L.K. et al., "Matrix-Assisted Secondary Ion Mass Spectra of Biological Compounds," Analytical Chemistry, 1981, vol. 53 (1), pp. 109-113.
Losa R., et al., "Determination of Thiamine and Its Phosphorylated Forms in Human Plasma, Erythrocytes and Urine by HPLC and Fluorescence Detection: A Preliminary Study on Cancer Patients," Journal of Pharmaceutical and Biomedical Analysis, 2005, vol. 37 (5), pp. 1025-1029.
Mascher H.J. et al., "High-Performance Liquid Chromatography Determination of Total Thiamin in Human Plasma," Methods in Enzymology, 1997, vol. 279, pp. 83-90.

(Continued)

*Primary Examiner* — Satyendra K Singh
(74) *Attorney, Agent, or Firm* — Foley & Lardner LLP

(57) ABSTRACT

Provided are methods for determining the amount of total thiamine in a body fluid sample using liquid chromatography and mass spectrometry. Total thiamine is converted to free thiamine by treatment with an acid phosphatase prior to thiamine separation and quantification.

9 Claims, 3 Drawing Sheets

(56) References Cited

PUBLICATIONS

Non-Final Office Action mailed Aug. 13, 2019 for U.S. Appl. No. 16/036,340, filed Jul. 16, 2018.
Non-Final Office Action mailed Dec. 2, 2013 for U.S. Appl. No. 13/724,839, filed Dec. 21, 2012.
Non-Final Office Action mailed Jan. 22, 2016 for U.S. Appl. No. 14/063,956, filed Oct. 25, 2013.
Non-Final Office Action mailed Sep. 23, 2010 for U.S. Appl. No. 11/869,657, filed Oct. 9, 2007.
Non-Final Office Action mailed Jun. 24, 2013 for U.S. Appl. No. 13/724,839, filed Dec. 21, 2012.
Patent Board Decision mailed May 15, 2018 for U.S. Appl. No. 13/724,839, filed Dec. 21, 2012.
Patent Board Decision—Examiner Affirmed mailed Aug. 27, 2015 for U.S. Appl. No. 11/869,657, filed Oct. 9, 2007.
Pinto E., et al., "Simultaneous Detection of Thiamine and its Phosphate Esters from Microalgae by HPLC," Biochemical and Biophysical Research Communications, 2002, vol. 291 (2), pp. 344-348.
Rindi G., et al., "Separation and Determination of Thiamine and Pyrithiamine in Biological Materials by Chromatography on Polyethylene Powder," Analytical Biochemistry, 1963, vol. 5, pp. 179-186.
Yamanaka K., et al., "Analysis of Thiamine in Dried Yeast by High-Performance Liquid Chromatography and High-Performance Liquid Chromatography/Atmospheric Pressure Chemical Ionization-Mass Spectrometry," Chromatographia, 1994, vol. 39 (1-2), pp. 91-96.
Zhao R., et al., "Reduced Folate Carrier Transports Thiamine Monophosphate: An Alternative Route for Thiamine Delivery into Mammalian Cells," American Journal of Physiology, 2002, vol. 282 (6), pp. C1512-C1517.

MASS SPECTROMETRY METHOD FOR MEASURING THIAMINE IN BODY FLUID

CROSS-REFERENCE TO RELATED PATENT APPLICATIONS

This application is a continuation of U.S. application Ser. No. 16/036,340, filed Jul. 16, 2018, now a U.S. Pat. No. 10,738,344, which is a continuation of U.S. application Ser. No. 13/724,839, filed Dec. 21, 2012, now abandoned, which is a continuation of U.S. application Ser. No. 11/869,657, filed Oct. 9, 2007, now abandoned, which is incorporated by reference herein in its entirety including all figures and tables.

FIELD OF THE INVENTION

The invention relates to the detection of vitamin B1 (thiamine).

BACKGROUND OF THE INVENTION

Thiamine, also known as vitamin B1, is a water-soluble vitamin that exists in the body as free thiamine and in one of several phosphorylated forms including thiamine monophosphate (ThMP), thiamine pyrophosphate (ThPP), thiamine triphosphate (ThTP), and adenosine thiamine triphosphate (AThTP). In human body, the primary vitamin B1 in serum and plasma is free thiamine while ThPP predominates in cellular components, for example blood cells. ThMP and ThTP only exist in very limited amounts (under detection level) in body fluid. The AThTP was recently discovered in *Escherichia coli* (Nature Chemical Biology 3, 211-212, 2007). Its existence and significance in human have not been reported at present.

Thiamine and its derivatives play an important role in the metabolism of lipids and carbohydrates. ThPP, also known as thiamine diphosphate (ThDP), is the major biologically active form of thiamine and is a required coenzyme for a number of enzymes involved in carbohydrate metabolism and nervous system function including the biosynthesis of lipids and acetylcholine. Thiamine-requiring enzymes include, for example, pyruvate dehydrogenase, α-ketoglutarate dehydrogenase, branched-chain α-ketoacid dehydrogenase, transketolase, and 2-hydroxyphytaoyl-CoA lyase.

Thiamine in food is easily decomposed by heat and particularly under alkaline conditions. After oral ingestion, thiamine is readily absorbed by both active transportation at low concentrations (<5 mg/dL) and passive diffusion at higher concentration levels. Phosphorylation in the jejunal mucosa produces ThPP.

Thiamine deficiency is frequently caused either by an inadequate intake of thiamine-rich foods (e.g., peas, spinach, liver, beef, and bananas), impaired absorption (genetic), over consumption of thiaminase-rich foods (e.g., raw fish and shellfish) or food high in anti-thiamine factors (e.g., tea and coffee), general malnutrition, or alcoholism. Thiamine deficiency results in a variety of diseases with a myriad of symptoms affecting virtually every system in the body. Beriberi, for example, is a condition induced by thiamine deficiency which is characterized by peripheral neuropathy resulting in abnormal reflexes, diminished sensation, muscle pain and weakness, and seizures. "Wet" beriberi affects the cardiovascular system, with peripheral edema and tachycardia due to congestive heart failure. The cerebral form of the disease may result in Wernicke's encephalopathy, Korsakoff's psychosis, or Wernicke-Korsakoff Syndrome.

SUMMARY OF THE INVENTION

The present invention relates to the detection and quantification of total thiamine in a body fluid sample. Phosphorylated thiamine in the body fluid is converted to free thiamine by hydrolysis using a phosphatase. The free thiamine is recovered by an organic solvent extraction and purified by liquid chromatography. Mass spectrometry (MS) is used to quantify the amount of free thiamine, which is related to the concentration of total thiamine present in the body fluid sample.

Accordingly, the invention provides a method for determining the amount of total thiamine in a body fluid sample by (i) removing soluble protein from the sample, (ii) treating the sample with an acid phosphatase to convert phosphorylated thiamine into free thiamine; (iii) performing an organic solvent extraction on the sample following the acid phosphatase treatment of step (ii); (iv) purifying the free thiamine by liquid chromatography from the aqueous phase that results from the organic solvent extraction of step (iii); and (v) determining the amount of free thiamine by mass spectrometry, wherein the amount free thiamine is related to the amount of total thiamine in the body fluid sample, and the amount of total thiamine in the body fluid sample is determined.

In preferred embodiments, soluble protein is removed in step (i) using acid precipitation. Suitable acids include, for example, perchloric acid, hydrochloric acid, sulfuric acid, nitric acid, boric acid, and acetic acid. Most preferably, soluble protein is removed using 7% perchloric acid. Following precipitation, the acid insoluble protein may be removed by any suitable method including, for example, filtration or centrifugation.

In preferred embodiments, a body fluid sample is obtained from a mammal, preferably a primate (e.g., a human), a dog, a cat, or a horse. Suitable body fluids include whole blood, plasma, serum, urine, saliva, tears, and cerebrospinal fluid.

In preferred embodiments, an phosphatase is used under acidic condition (pH 4.6+/−0.1) and the phosphatase reaction converts substantially all (e.g., at least 80%, 85%, 90%, 95%, 99%, or 100%) of the phosphorylated thiamine into free thiamine. In other embodiments, the phosphatase is an acid phosphatase including, for example, thiamine pyrophosphatase.

The organic solvent extraction comprises mixing an organic solvent with the aqueous bodily fluid for a sufficient time that lipophilic impurities dissolve in the organic solvent and the phosphatase reaction is terminated. In preferred embodiments of the organic solvent extraction, the organic solvent is tetrahydrofuran, benzene, toluene, diethyl ether, chloroform, ethyl acetate, or dichloromethane. Most preferably, the organic solvent is chloroform.

In one embodiment, the liquid chromatography is high performance liquid chromatography (HPLC). Preferably, the HPLC is reverse phase HPLC. More preferably, the HPLC utilizes a C18 analytical chromatography column. In another preferred embodiment, the HPLC utilizes a mobile phase gradient (e.g., a step gradient or a continuous gradient) comprising an acetic acid buffer and acetonitrile.

In one preferred embodiment, the thiamine-containing effluent of the HPLC column is directed, in an in-line format, into a mass spectrometry (MS) device where it is ionized to a parent ion in the MS device. One useful method of ionization is electrospray ionization. Preferably, the thiamine parent ion has a mass/charge ratio of 265.00±1.00. In one embodiment, the thiamine parent ion quantified by the MS operating in positive ion mode. In another embodiment, the thiamine parent ion is further isolated using a first MS quadrupole analyzer, followed by fragmentation into one or more thiamine daughter ions. One or more thiamine daughter ions are subsequently detected and/or quantified by the MS operating in positive ion mode. Preferably, the one or more thiamine daughter ions include an ion having a mass/charge ratio of 144.00±1.00 or 121.94±1.00. In one embodiment, the thiamine daughter ions are formed by collision induced dissociation using an inert gas. Preferable inert gases include, for example, argon, helium, and nitrogen.

In one embodiment, a separately detectable internal standard is added to the body fluid sample. Preferably, the internal standard is added to the body fluid prior to the first processing step. Preferred internal standards include, for example, pyrithiamine and isotopically labeled (e.g., deuterated, or carbon-13 labeled) thiamine or the corresponding salt forms. For methods in which pyrithiamine is used as an internal standard, preferably the pyrithiamine is ionized to parent ion having a mass/charge ratio (m/z) of 259.04+/−1.0 prior to the first MS detection or isolation. It is also preferable that the pyrithiamine parent ion is fragmented to a daughter ion having a mass/charge ratio of 122.00+/−1.0 m/z for detection and quantification by the second MS.

The term "operating in positive ion mode" refers to those mass spectrometry methods where positive ions are detected. Similarly, "operating in negative ion mode" refers to those mass spectrometry methods where negative ions are detected.

DETAILED DESCRIPTION OF THE INVENTION

Figure 1:
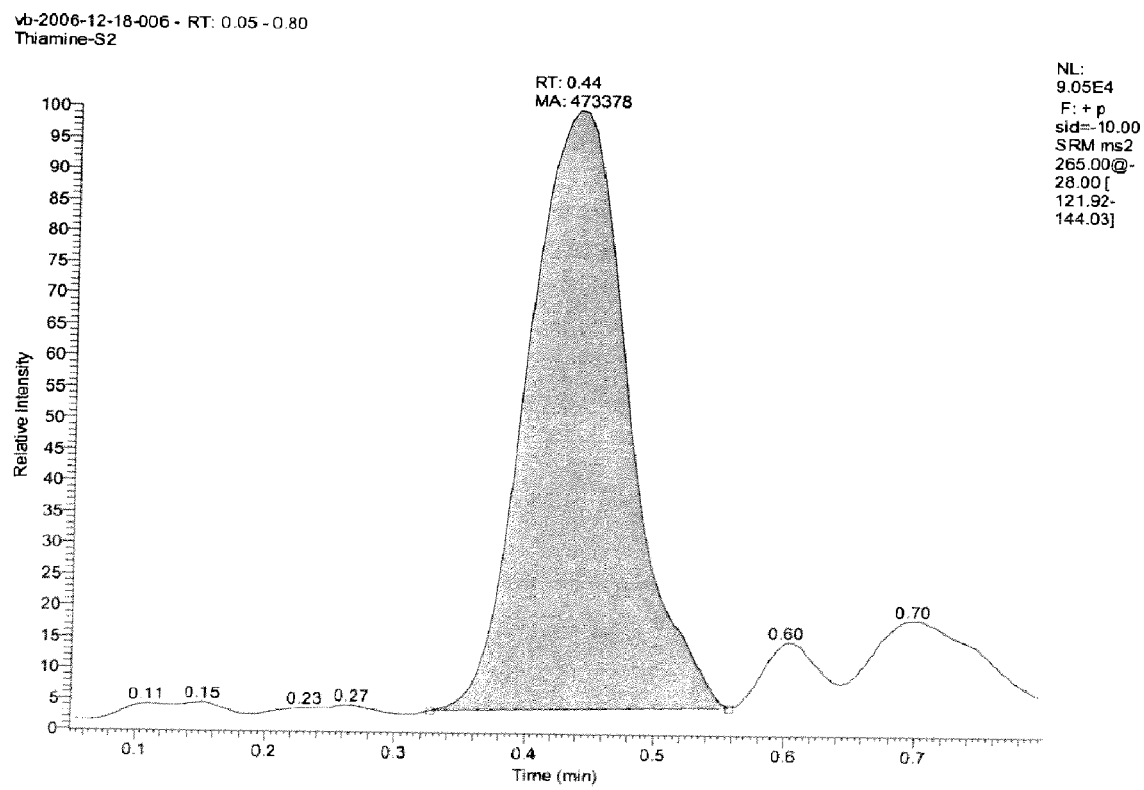
FIG. 1 is a chromatogram showing the elution of 15 nmol/L thiamine from an EDTA-plasma sample using the sample preparation and HPLC procedures described herein. Thiamine elutes with a peak retention time of about 0.44 minutes.

The present invention provides methods for determining the amount of total thiamine in a sample of body fluid (e.g., serum, plasma, and whole blood). The method first removes soluble protein (e.g., by acid precipitation), followed by an acid phosphatase treatment which converts phosphorylated thiamine into thiamine. The acid phosphatase reaction is terminated by an organic solvent (e.g., chloroform) extraction and the thiamine is purified using liquid chromatography; preferably high performance liquid chromatography. Thiamine is quantified using mass spectrometry. In preferred embodiments, the thiamine is quantified by tandem mass spectrometry (MS/MS) in which the thiamine is first ionized to a parent ion which is isolated by a first mass spectrometer. The isolated parent ion is then fragmented into one or more characteristic daughter ions and quantified by a second mass spectrometer.

The inventive method may be adapted to a high-throughput format. The assay offers enhanced sensitivity, specificity, and is accomplished in less time and with less sample preparation than required by other thiamine assays. In various embodiments the methods of the invention accurately quantify total thiamine concentrations as low as 6 nmol/L. Typically, however, total thiamine detected in plasma and serum is about 8-30 nmol/L and 78-185 nmol/L in whole blood.

The term "total thiamine" as used herein refers to all forms of thiamine present in a sample of body fluid. Specifically included in "total thiamine" are free thiamine, and thiamine converted from thiamine monophosphate (ThMP), thiamine pyrophosphate (ThPP), and thiamine triphosphate (ThTP).

The term "analytical column" as used herein refers to a chromatography column having sufficient chromatographic "plates" to effect a separation of materials in a sample that elute from the column sufficient to allow a determination of the presence or amount of an analyte. Such a column is often distinguished from an "extraction column," which has the general purpose of separating or extracting retained material from non-retained materials in order to obtain a purified sample for further analysis. A preferred analytical column is an HPLC column.

Sample Collection

The thiamine concentration may be assessed in any body fluid. Most conveniently, thiamine is assessed in whole blood or a blood fraction such as plasma, serum. Standard techniques for obtaining, processing, storing, and shipping these thiamine-containing body fluids may be used. It is well-known that thiamine is light-, and heat-sensitive so care should be taken throughout the sample collection and assay procedure to protect the sample against light and heat exposure that would result in significant thiamine degradation.

In preferred embodiments, plasma and serum samples are processed from whole blood within four hours of receipt by the laboratory. Desirably, the samples are maintained at about −10° C. to about −30° C. until assayed for thiamine. It is also preferred if the subject has fasted for about 12 hours prior to blood sampling. Further, it is desirable that the subject refrains for 24 hours prior to blood sampling from consuming alcohol, coffee, tea, raw fish, raw shell fish, and vitamin supplements containing thiamine Protein Removal Prior to performing the acid phosphatase reaction, it is desirable to remove potentially interfering molecules. One such processing step includes performing a protein removal step. The removal of potentially interfering proteins may be accomplished by any appropriate method including, for example, liquid chromatography, acid precipitation, filtration, centrifugation, and the like. Protein removal by filtration typically employs either spin filters or pressure filters having a pore size of ≤0.22 μm.

In a preferred embodiment, protein is removed from the sample by performing a protein precipitation reaction. This is achieved by adding a precipitating agent (e.g., an acid) to the body fluid sample, mixing the agent and the sample for a time and under conditions sufficient to cause protein precipitation, and then separating the precipitated proteins from the thiamine-containing solution. In a preferred embodiment, an equal amount of 7% aqueous perchloric acid is added to the body fluid sample, followed by vigorous mixing and incubation at 15° C. for about 5-30 minutes. The samples are centrifuges to pellet the protein and other acid-insoluble matter (e.g., 3000 rpm for 10 minutes at 2-8° C.), and the thiamine-containing supernatant is removed for further processing.

Acid Phosphatase Reaction

The present invention provides a method for detecting total thiamine in a single assay. The inventive method converts phosphorylated thiamine (e.g., ThMP, ThPP, and ThTP) into free thiamine in order that only a single thiamine species is detected and quantified. Conversion of phosphorylated thiamine into free thiamine may be done by any convenient method including, for example, treatment of the thiamine-containing sample with an acid phosphatase. Suitable acid phosphatases include, for example, those derived from plant sources (e.g., potato, sweet potato, and wheat germ), and mammalian sources (e.g., human and bovine) which is used at about 1-30 mg/ml, preferably about 10 mg/ml. It is desirable that the acid phosphatase reaction is run to substantial completion (i.e., that substantially all of the phosphorylated thiamine is hydrolyzed to free thiamine). Typically, the acid phosphatase reaction is performed under acidic condition (pH 4.6+/−0.1) at about 40° C. and is run for about one to two hours for serum and plasma samples or 12+ hours (e.g., overnight) for whole blood samples.

Organic Solvent Extraction

Following the acid phosphatase hydrolysis reaction, the body fluid sample contains a variety of salts, proteins (including the acid phosphatase enzyme), and other impurities, which desirably should be removed prior to mass spectrometry. Organic solvent extraction is a useful method to both terminate the hydrolysis reaction and remove lipophilic impurities from the thiamine-containing sample.

An organic solvent (e.g., chloroform) is added to the acid phosphatase reaction vessel in sufficient quantity and for a sufficient duration to terminate the enzymatic reaction. Typically, about 1-20 volumes (e.g., 5 volumes) of organic solvent is added, the solution is vigorously mixed, and the organic and aqueous phases are separated. Phase separation may be expedited by mild centrifugation (e.g., about 3000 rpm for about 10 minutes). The thiamine-containing aqueous phase is recovered for further processing and the organic phase is discarded.

Thiamine Separation by Liquid Chromatography

Following organic solvent extraction, the thiamine is further purified from the aqueous phase by liquid chromatography (LC) prior to quantification using mass spectrometry. Liquid chromatography removes aqueous impurities and may be used to concentrate the thiamine for detection. Traditional LC relies on chemical interactions between sample components (e g, thiamine) and a stationary phase such as a column packing. Laminar flow of the sample, mixed with a mobile phase, through the column is the basis for separation of the components of interest. The skilled artisan understands that separation in such columns is a partition process.

In one embodiment, the thiamine is separated using high pressure liquid chromatography (HPLC). The skilled artisan recognizes a variety of suitable HPLC columns, mobile phases, and HPLC conditions suitable for thiamine separation. Preferably, the HPLC is reverse phase HPLC and/or the HPLC column is a C18 analytical column. The skilled artisan also recognizes a variety of mobile phases and mobile phase combinations useful for reverse phase HPLC. Preferably, the elution from the HPLC column is driven by a binary step-gradient of aqueous ammonium acetate (10 mM) and acetonitrile (100%).

In various embodiments, one or more of the purification and/or analysis steps can be performed in an automated fashion. By careful selection of valves and connector plumbing, two or more chromatography columns can be connected as needed such that material is passed from one to the next without the need for any manual steps. In preferred embodiments, the selection of valves and plumbing is controlled by a computer pre-programmed to perform the necessary steps. Most preferably, the chromatography system is also connected in-line to the detector system, e.g., an MS system. Thus, an operator may place a tray of hydrolyzed and purified samples in an autosampler, and the remaining operations are performed under computer control, resulting in purification and analysis of all samples selected. In one embodiment, a diverter valve is placed in-line between the LC column and the interface with the MS. The diverter valve directs the LC effluent into a waste container until slightly prior to the time expected thiamine peak retention (e.g., peak retention time minus 0.1, 0.15, 0.2, or 0.25 minutes). This prevents the high salt solvent front and other impurities from being passed into the MS device.

As used here, "in-line" refers to a configuration in which the LC and the ionization/injection device for the first MS quadropole are functionally connected in order that the LC effluent passes directly into the first MS device. "In-line" configurations may include a selector valve such that the effluent from two or more LC columns may be directed individually into the MS device and, optionally, to a waste container. Such a configuration is useful for a high throughput system and reduces the analysis time required for a large number of samples. High throughput systems may be designed in which an autosampler initiates LC purifications on the two or more LC columns at staggered intervals. In this way, the purified thiamine peak is eluted from each LC column at a known interval. Preferably, the purified thiamine peaks eluting from the two or more LC columns are directed into the MS device in rapid succession, but with sufficient temporal separation that individual measurements are not compromised. Such a high throughput system reduces the amount of "idle-time" for MS detection attributable to the LC procedure which typically requires more time than the MS analysis.

By contrast, "off-line" refers to a configuration that requires manual intervention to transfer the LC effluent to the MS device. Typically, the LC effluent is captured by a fractionator and must be manually loaded into a MS device or into an autosampler for subsequent MS detection. Off-line configurations are useful, but less desirable because of the increased time required to process large numbers of samples.

Thiamine Analysis by Mass Spectrometry

Thiamine purified by LC is conveniently detected and quantified by mass spectrometry (MS). The thiamine-containing effluent from the LC is injected into an ionization chamber of the MS in which a first (parent) ion is produced. The parent ion may be detected directly in a first MS, or it may be isolated by the first MS, fragmented into characteristic daughter ions, and one or more of the daughter ions detected in a second MS (i.e., tandem MS).

The term "mass spectrometry" or "MS" as used herein refer to methods of filtering, detecting, and measuring ions based on their mass-to-charge ratio, or "m/z." In general, one or more molecules of interest are ionized, and the ions are subsequently introduced into a mass spectrographic instrument where, due to a combination of magnetic and electric fields, the ions follow a path in space that is dependent upon mass ("m") and charge ("z").

As used herein, the term "ionization" refers to the process of generating an analyte ion having a net electrical charge equal to one or more electron units. Negative ions are those having a net negative charge of one or more electron units, while positive ions are those having a net positive charge of one or more electron units.

The ions may be detected using several detection modes. For example, selected ions may be detected using a selective ion monitoring mode (SIM) which includes multiple reaction monitoring (MRM) or selected reaction monitoring (SRM). Alternatively, ions may be detected using a scanning mode.

Preferably, the mass-to-charge ratio is determined using a quadrupole analyzer. For example, in a "quadrupole" or "quadrupole ion trap" instrument, ions in an oscillating radio frequency field experience a force proportional to the DC potential applied between electrodes, the amplitude of the RF signal, and m/z. The voltage and amplitude can be selected so that only ions having a particular m/z travel the length of the quadrupole, while all other ions are deflected. Thus, quadrupole instruments can act as both a "mass filter" and as a "mass detector" for the ions injected into the instrument.

"Tandem mass spectrometry," or "MS/MS" is employed to enhance the resolution of the MS technique. In tandem mass spectrometry, a parent ion generated from a molecule of interest may be filtered in an MS instrument, and the parent ion subsequently fragmented to yield one or more daughter ions that are then analyzed (detected and/or quantified) in a second MS procedure.

Collision-induced dissociation ("CID") is often used to generate the daughter ions for further detection. In CID, parent ions gain energy through collisions with an inert gas, such as argon, and subsequently fragmented by a process referred to as "unimolecular decomposition." Sufficient energy must be deposited in the parent ion so that certain bonds within the ion can be broken due to increased vibrational energy.

By careful selection of parent ions using the first MS procedure, only ions produced by certain analytes of interest are passed to the fragmentation chamber to generate the daughter ions. Because both the parent and daughter ions are produced in a reproducible fashion under a given set of ionization/fragmentation conditions, the MS/MS technique can provide an extremely powerful analytical tool. For example, the combination of filtration/fragmentation can be used to eliminate interfering substances, and can be particularly useful in complex samples, such as biological samples.

The mass spectrometer typically provides the user with an ion scan; that is, the relative abundance of each m/z over a given range (e.g., 10 to 1200 amu). The results of an analyte assay, that is, a mass spectrum, can be related to the amount of the analyte in the original sample by numerous methods known in the art. For example, given that sampling and analysis parameters are carefully controlled, the relative abundance of a given ion can be compared to a table that converts that relative abundance to an absolute amount of the original molecule. Alternatively, molecular standards (e.g., internal standards and external standards) can be run with the samples, and a standard curve constructed based on ions generated from those standards. Using such a standard curve, the relative abundance of a given ion can be converted into an absolute amount of the original molecule. In certain preferred embodiments, an internal standard is used to generate a standard curve for calculating the quantity of thiamine. Numerous other methods for relating the presence or amount of an ion to the presence or amount of the original molecule are well known to those of ordinary skill in the art.

The skilled artisan will understand that the choice of ionization method can be determined based on the analyte to be measured, type of sample, the type of detector, the choice of positive versus negative mode, etc. Ions can be produced using a variety of methods including, but not limited to, electron ionization, chemical ionization, fast atom bombardment, field desorption, and matrix-assisted laser desorption ionization (MALDI), surface enhanced laser desorption ionization (SELDI), photon ionization, electrospray ionization, and inductively coupled plasma. Electrospray ionization is a preferred ionization method. The term "electrospray ionization," or "ESI," as used herein refers to methods in which a solution is passed along a short length of capillary tube, to the end of which is applied a high positive or negative electric potential. Solution reaching the end of the tube, is vaporized (nebulized) into a jet or spray of very small droplets of solution in solvent vapor. This mist of droplets flows through an evaporation chamber which is heated to prevent condensation and to evaporate solvent. As the droplets get smaller the electrical surface charge density increases until such time that the natural repulsion between like charges causes ions as well as neutral molecules to be released.

Desirably, the effluent of the LC is injected directly and automatically (i.e., "in-line") into the electrospray device. In preferred embodiments, the thiamine contained in the LC effluent is first ionized by electrospray into a parent ion of about 265.00±1.00 m/z. The first quadropole of the MS/MS is tuned to be a mass filter for the thiamine parent ion (and/or the internal standard).

Parent ion(s) passing the first quadrupole are then ionized and/or fragmented prior to passing into the second quadropole. In preferred embodiments, the ions are collided with a inert gas molecule in a process of collision-induced dissociation (CID). Suitable inert gases include, for example, argon, helium, nitrogen, etc. Desirably, the thiamine parent ion is fragmented into daughter ions having m/z=144.03±1.00 and/or m/z=121.94±1.00. It is these daughter ions that are subsequently detected.

Standards

It is desirable to use one or more standards for calibration and quantification purposes. Internal and external standards are commonly used for these purposes. Internal standards are typically analogs of the compound(s) of interest that are expected to react similarly during all extraction and quantification steps. A known amount of an internal standard is typically added to each sample early in the processing in order to account for any loss of compound during any processing step. External standards are typically consist of samples containing a known quantity of the compound of interest, or an analog, which are processed in parallel with the experimental samples. External standards are often used to control for the efficiency of the various processing steps. Finally, calibration standards are used to quantify the amount of the compound of interest in each experimental and external control sample. Typically, a series of calibration standards containing varying known amounts of the compound(s) of interest are injected directly into the detection device (i.e., the MS). Calibration standards are used to generate a standard curve, against which the experimental samples are quantified. These standards also may be used to determine limits of detection for any particular detection methodology.

Internal Standards

Typically, the internal standard is added in a known quantity to the sample of body fluid immediately after thawing and prior to the first extraction or purification step. A suitable internal standard that may be used is pyrithiamine (e.g., pyrithiamine hydrobromide; Sigma-Aldrich, Catalog No. P0256). Pyrithiamin, when subjected to the LC-MS-MS conditions described herein gives rise to a parent ion having m/z=259.04±1.00 and a daughter ion having m/z=122.00±1.00. Alternatively, deuterated or carbon-13 labeled thiamine may be used as an internal standard.

External Standards

Thiamine or any of its phosphorylated forms (e.g., ThMP, ThPP, ThTP, and AThTP) may be used as an external standard. Typically, the external standard is prepared in a medium that closely resembles the medium of the experimental samples and is processed in parallel with the experimental samples. The phosphorylated forms of thiamine are preferred as external standards in order to control for the efficiency of the acid phosphatase reaction. One useful medium is analyte-stripped and delipidized human serum (Biocell™; Biocell Labs, Carson, CA; catalog no. 1131-00).

Calibration Standards

Thiamine, the compound of interest, is preferably used as the calibration standard in order to create a calibration curve. Generally, the calibration curve covers thiamine concentrations from about the limit of detection to a concentration at least two-fold greater (preferably at least an order of magnitude greater) than the highest expected thiamine value in an experimental sample. When an internal standard is used in the experimental samples, it is desirable to add a similar amount of the internal standard to the calibration standards and to create a standard curve based on the ratio of the thiamine signal (e.g., peak area) to internal standard signal. This is referred to as the area ratio is useful to eliminate some inter-sample variability that may be present for calibration curves based solely on the thiamine concentration.

Blanks

Blanks are samples processed in parallel with the experimental samples and/or positive controls which contain a similar (or the same) medium as used to prepare the positive controls and/or is similar to the body fluid in which thiamine is being measured. One preferred medium useful as both a blank and as the medium for the positive controls is analyte-stripped and delipidized human serum (Biocell™; Biocell Labs, Carson, CA; catalog no. 1131-00). Another useful medium is thiamine-stripped serum (e.g., human serum). Another useful medium is a purely synthetic serum. Synthetic serums may consist solely of albumin dissolved in water or saline or may contain other components found in normal human serum. Most importantly, the medium used for the blanks, positive controls, and/or calibration standards is substantially free of thiamine (other than that added by the investigator). Preferably, the medium contains less than 6 nmol/L, and more preferably, less than 1-3 nmol/L.

The following examples serve to illustrate the invention. These examples are in no way intended to limit the scope of the invention.

Example 1. Blood Sampling, Initial Processing, and Storage

Subjects were restricted from alcohol, coffee, tea, raw fish, raw shellfish, and vitamins consumption for 24 hours before blood sample collection. An overnight fast was also required prior to blood sample collection.

For plasma samples, blood was collected in light-protected tubes containing EDTA or sodium heparin. Plasma was prepared within 4 hours of sample collection by centrifugation of whole blood at 800-1000×g for 8-10 minutes, at 2-8° C.

For serum samples, blood was collected in light-protected tubes and allowed to clot at about 2-8° C. for about 20-30 minutes, followed by centrifugation at 800-1000 xg for 8-10 minutes.

Immediately following collection and initial processing, serum, plasma, and whole blood samples were transferred to dark-brown polypropylene or polyethylene transport tubes or to neutral color polypropylene or polyethylene tubes that were wrapped in aluminum foil to protect the samples from light. The samples were then frozen at −10 to −30° C. until assay.

Example 2. Sample Preparation for HPLC Analysis

An internal standard (IS) working solution of 1.0 μg/mL of pyrithiamine hydrobromide (Sigma-Aldrich, Catalog No. P0256) was prepared by dissolving 25 mg of pyrithiamine hydrobromide in 25 ml of 0.01N aqueous HCl and then diluting that solution 1:1000 with deionized water.

The samples (e.g., blood, serum, or plasma) were thawed, vortexed, aliquoted (400 μl of serum or plasma, 800 μl of whole blood), and spiked with 100 μl (200 μl for whole blood sample) of the diluted pyrithiamine IS working solution.

External standard solutions of TPP were prepared. A 10 mM TPP stock solution was prepared in 0.01 N aqueous HCl which was diluted 1:1000 in deionized water. This solution was used to prepare external standard solutions of 350 nM, 175 nM, and 35 nM TPP in analyte-stripped, delipidized human serum (Biocell Labs; catalog no. 1131-00). A 400 μl aliquot of each external standard solution was spiked with 100 μl of IS working solution and processed in parallel with the experimental samples. The external standard solutions were used for quality control and to ensure that the acid phosphatase reaction was performed to substantial completion.

Blanks (i.e., negative controls) containing no thiamine were also prepared and processed in parallel with the experimental samples. Blanks contained Biocell™ and IS.

All samples (i.e., experimental samples, external standards, and blanks) were subjected to a protein precipitation by adding 400 μl (800 μl for whole blood samples) of 7% aqueous perchloric acid. The samples were mixed for about 5 minutes, centrifuged at 3500 rpm for 10 minutes at 2-8° C. 400 μl of supernatant from each sample was recovered for further processing.

Next, the supernatants were mixed with an equal volume of 1.0 M sodium acetate buffer (pH 4.6±0.1). 100 μl of acid phosphatase solution (10 mg/ml in deionized water; Sigma-Aldrich, Catalog No. P3752) was added, mixed, and incubated at 40° C. for 1-2 hours (for plasma and serum samples). Whole blood was incubated overnight.

The hydrolysis reaction was terminated by the addition of 2 ml chloroform, followed by a brief vigorous mixing, and centrifugation at 3000 rpm for 10 minutes. 400 μl of the aqueous phase (top layer) was transferred to a 96-well plate compatible with an autosampler injector for HPLC separation.

Example 3. Sample Purification Using HPLC

The sample mixtures produced in Example 2 were subjected to HPLC purification. Ten microliters of solution were injected onto Cohesive TLX LC system with a Luna C18(2), 50×2.0 mm, 5 μm HPLC column (Phenomenex, Catalog No. 00B-4252-B0)).

The elution from the HPLC column was driven by a binary step-gradient of aqueous ammonium acetate and acetonitrile at a flow rate of 0.8 mL/minute. The total duration for chromatograph is 240 seconds with a data acquisition window of 60 seconds. The mobile phase is altered as follows:

| Time After Sample Injection (sec) | % aqueous phase (10 mM ammonium acetate) | % organic phase (100% acetonitrile) |
| --- | --- | --- |
| 0 | 100% | 0% |
| 60 | 5% | 95% |
| 100 | 100% | 0% |
| 240 | ----- End of run ----- | |

Figure 2:
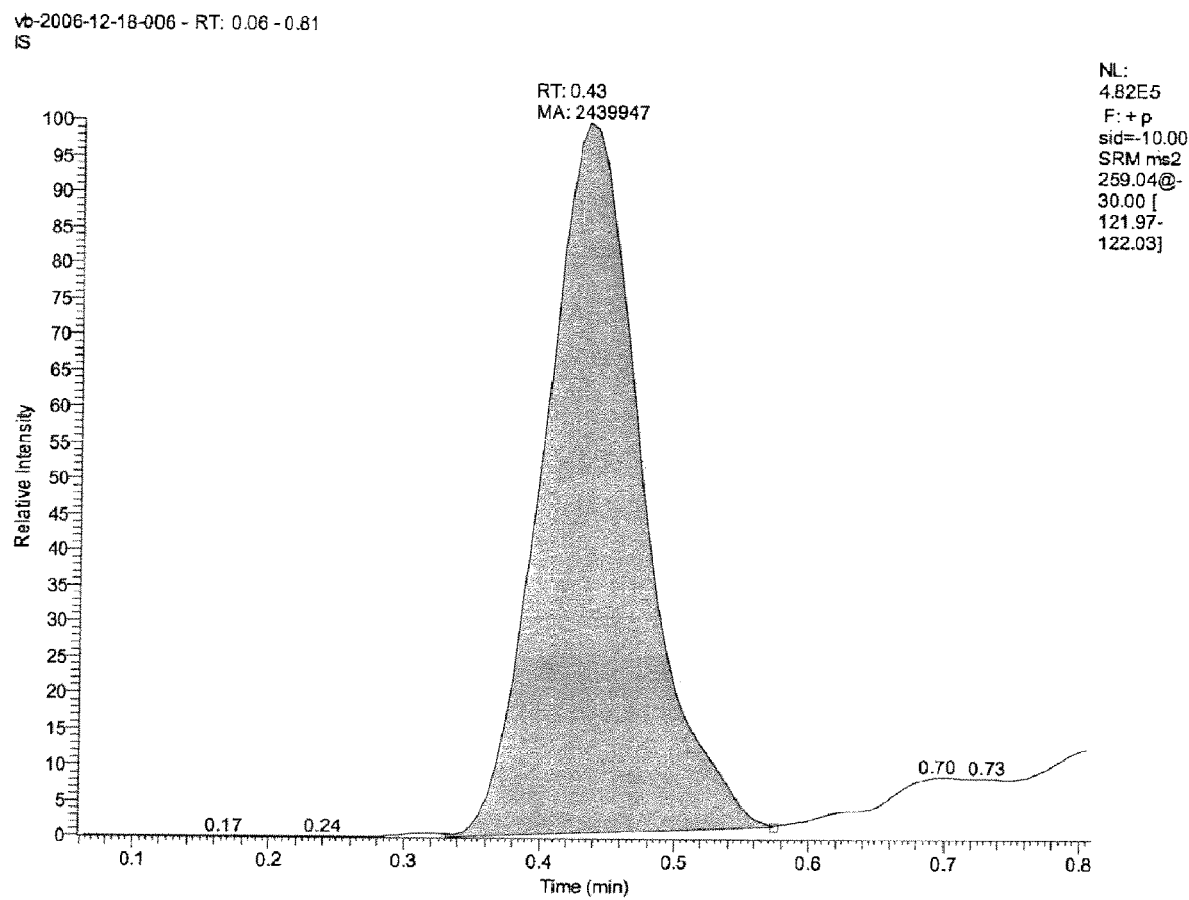
FIG. 2 is a chromatogram showing the elution of the internal standard (pyrithiamine) from a spiked EDTA-plasma sample using the sample preparation and HPLC procedures described herein. The internal standard elutes with a peak retention time of about 0.44 minutes.

The selected parameters for HPLC were as follows:
Injection volume: 10±4 μL
Autosampler tray temperature: 5±2° C.
Switch valve loop size: 200 μL As shown in FIGS. 1 and 2, thiamine and the IS co-eluted at about 0.43 minutes from an EDTA-plasma sample. The co-eluting thiamine and IS was then transferred to the MS/MS for quantification.

Example 4. Sample Quantification Using MS/MS

Detection of thiamine and the IS was accomplished by electrospray triplequad MS-MS system (Thermo Finnigan TSQ Quantum Ultra). The flow of liquid solvent from the analytical column entered the heated nebulizer interface of the MS/MS analyzer. The solvent/analyte mixture was first converted to vapor in the heated tubing of the interface. The analytes, contained in the nebulized solvent, were ionized. The ions passed through the orifice of the instrument and entered the first quadrapole. Quadrapoles 1 and 3 (Q1 and Q3) were the mass filters, allowing selection of ions based on their mass to charge ratio (m/z). Quadrapole 2 (Q2) was the collision cell, where ions were fragmented by collision with argon molecules.

The first quadrapole of the MS/MS (Q1) selected for ionized thiamine with an m/z of about 265.00 or the internal standard with an m/z of about 259.04 ("the parent ions").

The parent ions passed to the collision chamber (Q2), while ions with any other m/z collided with the sides of the quadrapole (Q1) and were destroyed. Ions entering Q2 were subjected to Collision-Induced Dissociation (CID) by colliding with argon. The daughter ions generated were passed into quadrapole 3 (Q3) for detection. Two distinct daughter ions were detected for thiamine: m/z=144.03 and m/z=121.94. A single daughter ion was detected for the IS having m/z=122.00. Quantification of sample thiamine is based on peak area ratio of two thiamine daughter ions over the single IS daughter ion acquired by selective reaction monitoring (SRM) in positive mode. The peak area ratio used for quantification was calculated by summing the peak areas of the two thiamine daughter ions (m/z 144.03 and 121.94) and dividing the result by the peak area of the IS daughter ion (m/z 122.00).

Selected MS/MS parameters were:
Scan type: positive ion SRM
Run time: 1.0±0.2 minutes
MS/MS transitions: thiamine (265.00 parent ion to 144.03 and 121.94 daughter ions) internal standard (259.04 parent ion to 122.00 daughter ion)
MS common parameters:
spray voltage: 3400
sheath gas: 54
aux gas: 20
capillary temperature: 250° C.
tube lens offset: 101
collision energy: 10
scan width: 0.05
scan time: 0.1
Q1 resolution: 0.2
Q2 resolution: 0.7

Example 5. Calibration and Standard Curves Using MS/MS

A stock solution of 10 mM thiamine in 0.01N aqueous HCl was prepared and diluted to 10 μM in deionized water. Calibration standards of 6 nM, 15 nM, 30 nM, 60 nM, 150 nM, 300 nM, and 600 nM, and a blank, each further containing a consistent amount of IS, were prepared by further dilution with analyte-stripped, delipidized human serum (Biocell Labs; catalog no. 1131-00). The calibration standards were treated the same way as the samples, as described above.

Figure 3:
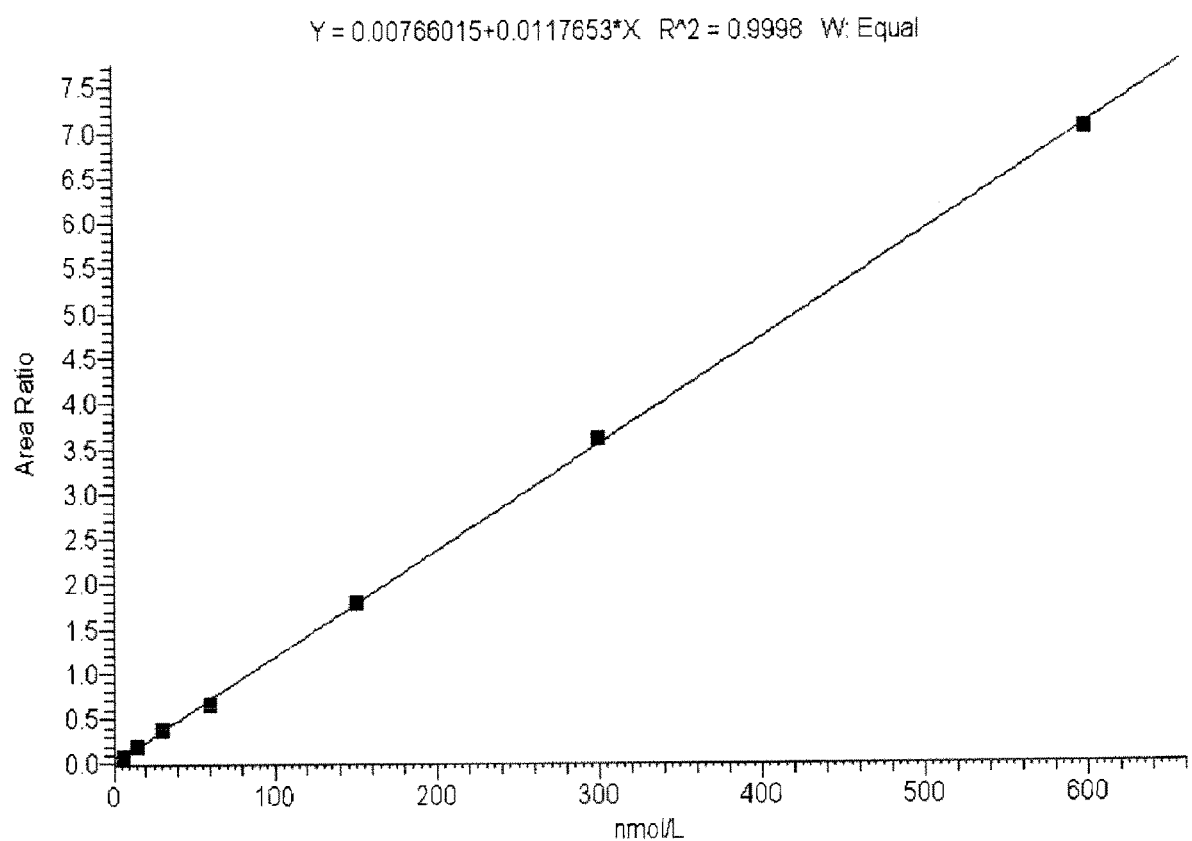
FIG. 3 is a graph showing a typical standard curve of thiamine purified and quantified using the LC/MS/MS method provided herein. The standard curve plots the ratio of the area of the thiamine peak to the area of the IS peak ("peak area ratio") versus the known concentration of thiamine in the calibration standards. Linear regression was performed on the data and the calculated regression line ($r^2$=0.9998) is shown.

The calibration standards were used to generate a standard curve of peak area ratio versus thiamine concentration. Peak area ratios for thiamine were calculated summing the peak area of two thiamine daughter ions (m/z 144.03 and 121.94) and dividing the result by the peak area of the IS daughter ion (m/z 122.00). The standard curve was generated using linear regression with 1/x weighting for data reduction. An acceptable calibration curve has a correlation coefficient ($R^2$) of 0.9950 or better. An standard curve generated by this method is shown in FIG. 3.

For all experimental, external control, and blank samples, the peak area ratios were calculated and plotted against the standard curve to quantify the thiamine concentration present in the sample. Calculations of the unknown concentration were performed using LCquan software in Xcalibur (Thermo Finnigan).

Unless otherwise defined, all technical and scientific terms used herein have the same meaning as commonly understood by one of ordinary skill in the art to which this invention be-longs.

The inventions illustratively described herein may suitably be practiced in the absence of any element or elements, limitation or limitations, not specifically disclosed herein. Thus, for example, the terms "comprising," "including," "containing," etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the invention claimed.

Thus, it should be understood that although the invention has been specifically disclosed by preferred embodiments and optional features, modification, improvement and variation of the inventions embodied therein herein disclosed may be resorted to by those skilled in the art, and that such modifications, improvements and variations are considered to be within the scope of this invention. The materials, methods, and examples provided here are representative of preferred embodiments, are exemplary, and are not intended as limitations on the scope of the invention.

All publications, patent applications, patents, and other references mentioned herein are expressly incorporated by reference in their entirety, to the same extent as if each were incorporated by reference individually. In case of conflict, the present specification, including definitions, will control.

What is claimed is:

1. A method for determining the amount of thiamine in a body fluid sample, comprising:
   (i) adding a pyrithiamine internal standard to the sample;
   (ii) purifying thiamine and the pyrithiamine internal standard from the body fluid sample by high performance liquid chromatography to form a purified thiamine and a purified pyrithiamine internal standard;
   (iii) ionizing and detecting the purified thiamine and the purified pyrithiamine internal standard by electrospray ionization tandem mass spectrometry with selected reaction monitoring in positive ion mode; and
   (iv) quantifying the amount of thiamine in the body fluid sample by analyzing fragmented ions using the tandem mass spectrometry, wherein the amount of total thiamine in the sample is determined based on the comparative abundance of daughter ions generated from thiamine that have a mass/charge ratio of 144.03+1.0 and 121.94+1.0, relative to the abundance of a daughter ion generated from pyrithiamine internal standard that has a mass/charge ratio of 122.00±1.0.

2. The method of claim 1, the method further comprising removing soluble protein from the body fluid sample prior to step (ii).

3. The method of claim 2, wherein soluble protein is removed by treating said body fluid sample with an acid.

4. The method of claim 1, the method further comprising incubating the body fluid sample with an acid phosphatase to convert phosphorylated thiamine to thiamine.

5. The method of claim 4, wherein the incubation is carried out at a pH of about 4.6±0.1.

6. The method of claim 4, wherein the incubation is carried out at a temperature of about 40° C.

7. The method of claim 4, wherein the incubation is carried out between about 1 and about 2 hours.

8. The method of claim 1, wherein the thiamine in the sample is ionized to a parent ion having a mass/charge ratio of 265.00 ±1.0.

9. The method of claim 1, wherein the pyrithiamine internal standard is ionized to a parent ion having a mass to charge ratio of 259.04±1.0.

* * * * *